(12) United States Patent
Krishna et al.

(10) Patent No.: US 11,957,769 B2
(45) Date of Patent: Apr. 16, 2024

(54) POLYHYDROXY FULLERENE SUNSCREEN ACTIVE AGENTS AND COMPOSITIONS

(71) Applicant: THE CLEVELAND CLINIC FOUNDATION, Cleveland, OH (US)

(72) Inventors: Vijay Krishna, Cleveland Heights, OH (US); Sanjay Anand, Cleveland, OH (US); Edward Maytin, Cleveland, OH (US); Stephen Grobmyer, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 355 days.

(21) Appl. No.: 17/182,093

(22) Filed: Feb. 22, 2021

(65) Prior Publication Data

US 2021/0251860 A1   Aug. 19, 2021

Related U.S. Application Data

(62) Division of application No. 16/075,854, filed as application No. PCT/US2017/016669 on Feb. 6, 2017, now Pat. No. 10,925,817.

(60) Provisional application No. 62/290,997, filed on Feb. 4, 2016.

(51) Int. Cl.
| | |
|---|---|
| *A61K 8/19* | (2006.01) |
| *A61K 8/11* | (2006.01) |
| *A61K 8/44* | (2006.01) |
| *A61Q 17/04* | (2006.01) |

(52) U.S. Cl.
CPC .................. *A61K 8/19* (2013.01); *A61K 8/11* (2013.01); *A61K 8/44* (2013.01); *A61Q 17/04* (2013.01); *A61K 2800/56* (2013.01)

(58) Field of Classification Search
CPC ... A61K 8/19; A61K 8/11; A61K 8/44; A61K 2800/56; A61Q 17/04
See application file for complete search history.

(56) References Cited

U.S. PATENT DOCUMENTS

| | | | |
|---|---|---|---|
| 7,195,754 B1 | 3/2007 | Glatkowski et al. | |
| 2006/0134095 A1* | 6/2006 | Ito | A61K 8/19 424/125 |
| 2007/0202413 A1 | 8/2007 | Wudl et al. | |
| 2011/0112232 A1 | 5/2011 | Krishna et al. | |
| 2012/0122695 A1 | 5/2012 | Naseri et al. | |

FOREIGN PATENT DOCUMENTS

| | | |
|---|---|---|
| EP | 2123288 A1 | 11/2009 |
| JP | H09278625 A | 10/1997 |
| WO | 2006/028297 A1 | 3/2006 |
| WO | 2008/118960 A2 | 10/2008 |

OTHER PUBLICATIONS

Australian Examination Report for corresponding Australian Serial No. 2017214687, dated Sep. 9, 2019, pp. 1-4.
Database GNPD [Online] MINTEL; Jan. 2015, Anonymous: "Face Serum", XP002768598, Database accession No. 2914573.
Database GNPD [Online] MINTEL; Jul. 2015, Anonymous: "Blanc Sun Protector SPF 50+/PA+++", XP002768600, Database accession No. 3310497.
Database GNPD [Online] MINTEL; Mar. 2008, Anonymous: "Brightening Day Lotion", XP002768599, Database Accession No. 872971.
Krishna, Vijay, et al. "Mechanism of enhanced photocatalysis with polyhydroxy fullerenes." Applied Catalysis B: Environmental 79.4 (2008): 376-381.
Krishna, Vijay, et al. "Polyhydroxy Fullerenes for Non-Invasive Cancer Imaging and Therapy." Small 6.20 (2010): 2236-2241.
Lu, Xing, et al. "Current status and future developments of endohedral metallofullerenes." Chemical Society Reviews 41.23 (2012): 7723-7760.
Lu, Xing, et al. "Recent progress in the chemistry of endohedral metallofullerenes." Chemical Communications 50.94 (2014): 14701-14715.
Nanot, S., N. A. Thompson, J.-H. Kim, X. Wang, W. D. Rice, E. H. Hároz, Y. Ganesan, C. L. Pint, and J. Kono, "Single-Walled Carbon Nanotubes" (Book Chapter), in: Handbook of Nanomaterials, edited by R. Vajtai (Springer, Berlin, 2013), pp. 105-146.
Reichrath, Jörg, ed. Sunlight, vitamin D and skin cancer. Springer, 2015.
Saitoh, Yasukazu, et al. "Super-highly hydroxylated fullerene derivative protects human keratinocytes from UV-induced cell injuries together with the decreases in intracellular ROS generation and DNA damages." Journal of Photochemistry and Photobiology B: Biology 102.1 (2011): 69-76.
Xiao, Li, et al. "Antioxidant effects of water-soluble fullerene derivatives against ultraviolet ray or peroxylipid through their action of scavenging the reactive oxygen species in human skin keratinocytes." Biomedicine & pharmacotherapy 59.7 (2005): 351-358.
Ye, Shefang, et al. "Polyhydroxylated fullerene attenuates oxidative stress-induced apoptosis via a fortifying Nrf2-regulated cellular antioxidant defence system." International journal of nanomedicine 9 (2014): 2073.
Yin, Jun-Jie, et al. "The scavenging of reactive oxygen species and the potential for cell protection by functionalized fullerene materials." Biomaterials 30.4 (2009): 611-621.

* cited by examiner

*Primary Examiner* — Aradhana Sasan
(74) *Attorney, Agent, or Firm* — TAROLLI, SUNDHEIM, COVELL & TUMMINO L.L.P.

(57) ABSTRACT

Sunscreen compositions comprising a dermatologically acceptable carrier and a polyhydroxy fullerene compound are described. The sunscreen compositions can be used to protect a substrate such as the skin of a subject from the effects of ultraviolet radiation.

3 Claims, 5 Drawing Sheets

POLYHYDROXY FULLERENE SUNSCREEN ACTIVE AGENTS AND COMPOSITIONS

CONTINUING APPLICATION DATA

This application is a Divisional Patent Applications of U.S. patent application Ser. No. 16/075,854, filed Aug. 6, 2018, which is a 371 National Phase filing of PCT/US2017/016669, filed Feb. 6, 2017, which claims the benefit of U.S. Provisional Patent Application Ser. No. 62/290,997, filed Feb. 4, 2016, the disclosures of each are hereby incorporated by reference herein.

GOVERNMENT FUNDING

This invention was made with government support under Army Grant #W81XWH-15-1-0580 awarded by the U.S. Department of Defense. The government has certain rights in the invention.

BACKGROUND

Every year, over one million new cases of skin cancer are diagnosed in the U.S., outnumbering the total number of all other cancer diagnoses combined, imposing an annual economic burden of $8.1 billion for skin cancer treatment. Exposure to UV radiation is the most common, and also the most preventable, cause of skin cancers. Skin damage with UV exposure occurs through at least two mechanisms: (i) direct damage to DNA, mainly from UVB (280-320 nm), and (ii) production of free radicals from UVA (320-400 nm), which destroy intracellular components including DNA, membranes, and proteins.

Sunscreens are the first step in skin cancer prevention. Sunscreen agents include both organic sunscreens and inorganic sunscreens. Inorganic sunscreens include inorganic particles which provide protection to the skin by directly blocking solar radiation. Examples of inorganic sunscreens include zinc oxide and titanium dioxide. However, a problem with inorganic sunscreens is that they give the skin an unnatural whiteness when applied at effective concentrations.

Organic sunscreen compounds are organic compounds which act by absorbing solar radiation at a particular range of wavelengths, and then emitting them at a different, less harmful wavelength. Organic sunscreens are categorized into UV-A sunscreens and UV-B sunscreens, depending on their absorption wavelength. The most common UV-A sunscreens are those of the dibenzoylmethane class. UV-B organic sunscreens include those based on benzophenone, cinnamic acid, salicylic acid, and diphenyl acrylic acid. However, in order to have sunscreen protection over the full range of harmful wavelengths, sunscreen compositions must include both UV-A sunscreen and UV-B sunscreen compounds, which can increase the cost and aggravate stability problems.

Current organic sunscreen formulations have multiple active ingredients (AIs) and suffer from ephemeral efficacy (requiring frequent reapplication), poor stability, and a tendency toward irritation and photo-allergies. Common organic UV-absorbers, such as avobenzone and octisalate, are easily degraded by UV and need stabilizers to function properly. Bens G, Sunscreens, in Sunlight, Vitamin D and Skin Cancer, J. Reichrath, Editor. 2014, Landes Bioscience and Springer Science+Business Media, LLC: New York. p. 429-463. Similarly, antioxidants, such as homosalate, are degraded by radicals or excited electrons generated from the UV absorbers. Several common AIs including oxybenzone and homosalate are reported to be endocrine disruptors and to cause skin allergy. Krause et al., Int J Androl, 35(3): p. 424-36 2012. Recent long-term studies have shown that sunscreen AIs such as oxybenzone reduce fertility in humans Certain AIs, such as retinyl palmitate used for reducing UV-induced skin aging, may even increase skin cancer risk. National Toxicology Program, Natl Toxicol Program Tech Rep Ser. (568):1-352 (2012). These limitations appear to contribute to the failure of current sunscreens in reducing the incidence of skin cancer. In addition, a recent study suggests that current sunscreens, with optimal application, provide only partial protection against UV-induced melanoma. Viros et al., Nature, 511(7510): p. 478-82 (2014). Further, the traditional antioxidants used in the sunscreens have major drawbacks of a) monofunctionality, i.e., each type of antioxidant is active against only a specific type of free radical such as gallocatechin for superoxide; b) low capacity, i.e., neutralizes only one free radical per molecule of antioxidant; c) low stability, i.e., antioxidants such as EGCG undergo auto-oxidation, forming dimers with concomitant generation of free radicals; and d) failure to activate Nrf2; the latter, also called nuclear factor erythroid 2-related factor, is an essential transcription factor that regulates expression of phase II antioxidants and detoxifying enzymes, thereby decreasing inflammation and preventing skin carcinogenesis. Accordingly, there remains a need for more effective sunscreen compositions, and particularly sunscreen agents that can provide effective sunscreen protection without requiring the use of multiple active agents, with good stability, and at relatively low concentration.

SUMMARY OF THE INVENTION

The present invention utilizes a novel, safe, multifunctional active ingredient called polyhydroxy fullerenes (PHF) for next-generation sunscreens. PHF absorbs both UVB and UVA, and is a powerful antioxidant. The innovative use of PHF as the AI in sunscreen overcomes the concerns associated with traditional AIs in current sunscreen formulations.

Polyhydroxy fullerenes (PHF) are water-soluble form of fullerenes. Fullerenes are spherical cages made of carbon atoms with a general formula of $C_{2n}$, where n can range from 10 to 270. The molecular formula for an unmodified PHF is $C_{2n}(OH)_x$; where x is in the range of 12 to 40.

PHF is a water-soluble, biocompatible and biodegradable molecule with excellent antioxidant properties. Krishna et al., Small, 6(20): p. 2236-2241 (2010). PHF is a broad spectrum UV absorber (i.e., it absorbs both UVB and UVA) with its critical wavelength of 381 nm and UVA/UVB ratio of 1.6 exceeding the FDA minimum limit of 370 nm and 0.91, respectively. The inventors have shown that PHF absorbs UV without generating free radicals (Krishna et al., Applied Catalysis B-Environmental, 79(4): p. 376-381 (2008), and can catalytically neutralize different types of free radicals (superoxide, nitric oxide, etc.), without any change to its molecular structure. Yin et al., Biomaterials, 30(4): p. 611-21 (2009). PHF activates the Nrf2 pathway to fortify the body's natural antioxidant system and alleviate allergies. Ye et al., Int J Nanomedicine, 9: p. 2073-87 (2014). The inventors engineered the PHF molecular structure to further enhance its antioxidant activity. See U.S. Pat. No. 9,084,989. Most importantly, PHF represents an effective, multifunctional sunscreen agent that could replace the multiple AIs in current sunscreens. This combined UV-absorber and antioxidant is simpler, safer, and more stable than current sunscreen formulations.

The inventors have discovered that PHF is a multifunctional active ingredient for sunscreen with superior UV protection properties. The in vitro and in vivo studies support use of PHF as a sunscreen active ingredient. Further, they have demonstrated that PHF can be easily incorporated in a model sunscreen formulation.

DETAILED DESCRIPTION OF THE INVENTION

The present invention provides a sunscreen composition, comprising a dermatologically acceptable carrier and a fullerene compound according to the formula $C_{2n}(OH)_t(NH_2)_v(COOH)_w(COOM)_xO_yM_z$, wherein M is an alkali metal, alkaline earth metal, transition metal, post-transition metals or lanthanides, n is a number ranging from 10 to 270, t is number ranging from 0 to 60, v is a number ranging from 0 to 60, w is a number ranging from 0 to 60, x is a numbering ranging from 0 to 60, y is a number ranging from 0 to 30, and z is a number ranging from 0 to 30. The present invention also provides methods of using the sunscreen composition to protect a substrate such as the skin of a subject from the effects of ultraviolet radiation.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

The recitations of numerical ranges by endpoints include all numbers subsumed within that range (e.g., 1 to 5 includes 1, 1.5, 2, 2.75, 3, 3.80, 4, 5, etc.).

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

A "sunscreen composition" as used herein, is meant to include a composition for topical application to sun-exposed areas of the skin and/or hair of mammals, especially humans. Such a composition may be generally classified as leave-on or rinse off, and includes any product applied to a human body including an active agent that protects the skin against UV-induced damage, and includes products that also improving appearance, cleansing, odor control or provide improved general aesthetics.

The term "dermatologically acceptable", as used herein, means that the compositions or components described are suitable for use in contact with human skin without risk of toxicity, incompatibility, instability, allergic response, and the like.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human. A subject in need of protection is a subject who is likely to be exposed to strong sunlight with potentially damaging UV radiation in the near future.

The language "effective amount" or "protective amount" refers to a nontoxic but sufficient amount of the composition used in the practice of the invention that is effective to decrease or prevent skin injury from exposure to sunlight and/or ultraviolet radiation. That result can be reduction and/or alleviation of the signs, symptoms, or other results from exposure to sunlight and/or ultraviolet radiation. An appropriate therapeutic amount in any individual case may be determined by one of ordinary skill in the art using routine experimentation.

Polyhydroxy Fullerenes

Figure 1:
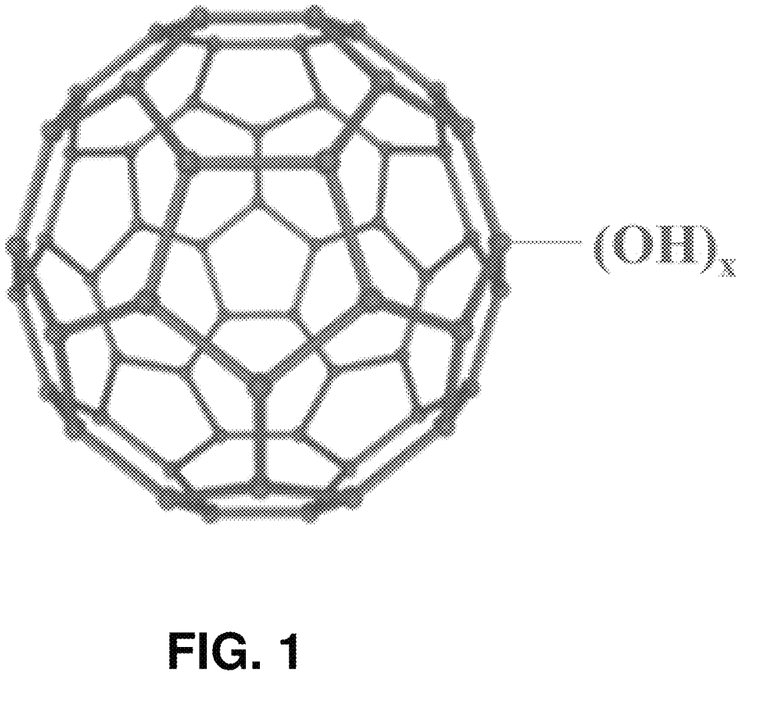
FIG. 1 provides a schematic representation of the chemical structure of a polyhydroxy fullerene (PHF) molecule (x=12 to 42).

Polyhydroxy fullerenes (PHF) are water-soluble form of fullerenes. The structure of unmodified polyhudroxyfullerenes is shown in FIG. 1. Fullerenes are spherical cages made of carbon atoms with a general formula of $C_2$—, where n can range from 10 to 270. The molecular formula for a relatively unmodified PHF is $C_{2n}(OH)_tO_yM_z$; where M is an alkali metal, alkaline earth metal, or transition metal; t is in the range of 8 to 60; y is in the range of 0 to 30; and z is in the range of 0 to 30.

The present invention is directed to PHF compositions that have the ability to absorb ultraviolet radiation, and exhibit an electron scavenging ability. The functionality of PHF influences its electron scavenging ability. PHFs commonly contain functional groups such as hydroxyl, hemiketal, epoxide and carbonyl groups that modify the electronic properties of the PHFs. It was discovered that PHFs which have a low ratio (≤0.3) of non-hydroxyl functional groups to hydroxyl functional groups have enhanced electron scavenging ability, whereas PHFs that display a ratio higher than 0.3 have decreased electron scavenging ability.

PHFs can be of a single size or can be mixtures of different fullerene sizes. The fullerene cage can be $C_{28}$, $C_{32}$, $C_{44}$, $C_{50}$, $C_{58}$, $C_{60}$, $C_{70}$, $C_{84}$, $C_{250}$, $C_{540}$, or any other fullerene. These correspond to polyhydroxy fullerenes of the claimed invention wherein n is 14, 16, 22, 25, 29, 30, 35, 42, 125, and 270, respectively. The PHFs have an average of about 1.25 to 3 C atoms per OH group, which is equivalent to about 27 to about 48 OH groups on a $C_{60}$ cage. The PHFs are often $C_{60}$ molecules due to their commercial availability, but other fullerene cages such as $C_{70}$, $C_{82}$ or their mixtures or other PHFs can be used in various embodiments of the invention. The PHFs have C—C single bonds that can be observed by Fourier transform infrared spectroscopy (FTIR). Other functional groups are primarily carbons of a hemiketal and carbonyl structure. PHFs can also contain epoxy groups and ester groups.

In one aspect, the present invention provides a sunscreen composition, comprising a dermatologically acceptable carrier and a fullerene compound according to the formula $C_{2n}(OH)_t(NH_2)_v(COOH)_w(COOM)_xO_yM_z$, wherein M is an alkali metal, alkaline earth metal, transition metal, post-transition metal or lanthanide, n is a number ranging from 10 to 270, t is number ranging from 0 to 60, v is a number ranging from 0 to 60, w and x are a number ranging from 0 to 60, y is a number ranging from 0 to 30, and z is a number ranging from 0 to 30. The number of fullerene carbons (C) hydroxyl (OH), amine ($NH_2$), carboxyl (COOH), metal carboxylate (COOM), oxygen (O) and metal (M) groups can all vary based on the ranges provided.

In some embodiments, the polyhydroxy fullerene is a compound according to the formula $C_{2n}(OH)_tO_yM_z$, which corresponds to the broader formula wherein v, w, and x are 0. In other embodiments, the polyhydroxy fullerene is a compound according to formula $C_{2n}(OH)_t$, which corresponds to the broader formula wherein t is 1 to 60, and v, w, x, y, and z are 0. In further embodiments, the polyhydroxy fullerene is a compound according to the formula $C_{2n}(OH)_t(NH_2)_vO_yM_z$, which corresponds to the broader formula wherein w and x are 0. In yet further embodiments, the polyhydroxy fullerene is a compound according to the formula $C_{2n}(OH)_t(COOH)_wO_yM_z$, which corresponds to the broader formula wherein v and x are 0. In additional embodiments, the polyhydroxy fullerene is a compound according to the formula $C_{2n}(OH)_t(COOM)_xO_yM_z$, which corresponds to the broader formula wherein v and w are 0.

The number of hydroxyl (OH), amine ($NH_2$), carboxyl (COOH), metal carboxylate (COOM), oxygen (O) and metal (M) groups can all vary. For example, for hydroxyl groups, amine groups, carboxyl groups, and metal carboxylate groups, the number can range from 0 to 60, 1 to 60, 8 to 60, 12 to 60, 20 to 60, 0 to 50, 1 to 50, 8 to 50, 12 to 50, 20 to 50, 0 to 40, 1 to 40, 8 to 40, 12 to 40, 20 to 40, 0 to 30, 1 to 30, 8 to 30, 12 to 30, or 20 to 30, or any other ranges within 0 to 60. For the oxygen and metal groups, the number can range from 0 to 30, 1 to 30, 4 to 30, 8 to 30, 12 to 30, 0 to 20, 1 to 20, 4 to 20, 8 to 20, 12 to 20, 0 to 10, 1 to 10, and 4 to 10.

Other potential structures for functionalized polyhydroxy fullerenes are also within the scope of the present invention. In some embodiments, the polyhydroxyfullerenes have a formula of $C_{2n}(OH)_tO_yM1_aM2_b$; where M1 and M2 are different alkali metals, alkaline earth metals, transition metals, post-transition metal or lanthanide; t is in the range of 0 to 60; y, a and b are in the range of 0 to 30.

In some embodiments, the polyhydroxy fullerenes include carbon or polymer strands bound to the surface of the fullerene cage. The carbon or polymer strands can include polyethylene, polyethylene glycol, polyanhydrides, polyesters, and polyolefins. For example in some embodiments, $C_{2n}[C_mO_pH_q](OH)_tO_yM_z$; where $(OH)_tO_yM_z$ are attached to fullerene cage via the one or more carbon or polymer chains $[C_mO_pH_q]$; m is in the range of 1 to 30 and p is in the range of 0 to 15, q is in the range of 2 to 60; n is in the range of 10 to 270, M is an alkali metal, alkaline earth metal, transition metal, post-transition metal or lanthanide; t is in the range of 0 to 60; y, z are in the range of 0 to 30. In other embodiments, the polyhydroxy fullerene is a compound according to $C_{2n}[C_mO_pH_q](COOH)_r(COOM)_s(OH)_tO_yM_z$; where carboxylic acid or metal salts are attached directly to fullerene cage or via the one or more carbon or polymer chains $[C_mO_pH_q]$; m is in the range of 1 to 30 and p is in the range of 0 to 15, q is in the range of 2 to 60; n is in the range of 10 to 270, r, s and t are in the range of 0 to 60; M is an alkali metal, alkaline earth metal, transition metal, post-transition metal or lanthanide; x is in the range of 0 to 60; y, z are in the range of 0 to 30. In further embodiments, the polyhydroxy fullerene is a compound according to $C_{2n}$ $[C_mO_pH_q](OH)_t(NH_2)_vO_yM_z$; where amine groups are attached directly to fullerene cage or via the one or more carbon or polymer chains $[C_mO_pH_q]$; m is in the range of 1 to 30 and p is in the range of 0 to 15, q is in the range of 2 to 60; n is in the range of 10 to 270, t is in the range of 0 to 60, v is in the range of 1 to 60, M is an alkali metal, alkaline earth metal, transition metal, post-transition metal or lanthanide; and y and z are in the range of 0 to 30.

In some embodiments, the invention provides a sunscreen composition comprising a dermatologically acceptable carrier and a polymer-bearing fullerene compound according to the formula $C_{2n}[C_mO_pH_q](OH)_v(COOH)_w(COOM)_xO_yM_z$, wherein M is an alkali metal, alkaline earth metal, transition metal, post-transition metal or lanthanide; n is a number ranging from 10 to 270, the one or more polymer chains $[C_mO_pH_q]$ in which m is in the range of 1 to 30 and p is in the range of 0 to 15, q is in the range of 2 to 60, v is number ranging from 0 to 60, w is a number ranging from 0 to 60, x is a numbering ranging from 0 to 60, y is a number ranging from 0 to 30, and z is a number ranging from 0 to 30.

Any of the above functionalized fullerenes can be prepared as endohedral metallofullerenes. See for example Lu et al., Chem Commun (Camb)., 50(94), pp. 14701-15 (2014), and Lu et al., Chem Soc Rev., 41(23), pp. 7723-60 (2012), the disclosures of which is incorporated herein by reference. Endohedral metallofullerenes have been made using a variety of different metals and rare earth metals, such as gadolinium, scandium, scandium-titanium, samarium, yttrium, neodymium, dysprosium, erbium, and lutetium. For example, $Gd@C_{60}$, $Gd_3N@C_{60}$, and $Sc_3N@C_{80}$ are typical endohedral fullerenes.

Polyhydroxy fullerenes (PHF) may be synthesized by synthetic routes that include processes similar to those well known in the chemical arts, particularly in light of the description contained herein. See for Example U.S. Pat. No. 9,084,989, and U.S. Patent Publication No. 2007/0202413, the disclosures of which are incorporated herein by reference. A number of fullerenes are also commercially available. See for example the Fullerene Supplier Database provided online by Nanowerk™.

The sun protection factor (SPF rating) is a measure of the fraction of sunburn-producing UV rays that reach the skin. For example, "SPF 15" means that ¹⁄₁₅th of the burning radiation will reach the skin, assuming sunscreen is applied evenly at a thick dosage of 2 milligrams per square centimeter ($mg/cm^2$). A user can determine the effectiveness of a sunscreen "by multiplying the SPF factor by the length of time it takes for him or her to suffer a burn without sunscreen. The PHF-based sunscreens described herein are both UVB and UVA absorbers, and can therefore also labeled with "SPFXX" (for UVB) and "Broad spectrum" (for UVA).

Sunscreen compositions according to the present invention can be formulated to achieve a variety of different SPFs. For example, the sunscreen formulations can have an in vitro or in vivo SPF of at least 5, 10, 15, 20, 25, 30, 35, 40, 45, 50, 55, 60, 65, 70, 75, 80, 85, 90, 95, 100, 105, 110, 115, 120, 125, 135, 150, 175, 200, 225, 250, 300. 325, 350, or higher (or in a range between any of these values).

Compositions of the present invention may, according to certain embodiments, be essentially free of UV-absorbing sunscreen agents other than PHF. By "essentially free of non-PHF UV-absorbing sunscreen agents," it is meant that, in this embodiment, the compositions do not contain non-PHF UV-absorbing sunscreen agents in an amount effective to provide the compositions with an SPF of greater than 2. For example, the compositions of the invention will contain about 0.5% or less, or about 0.1% or less, of such non-PHF UV-absorbing sunscreen agents. The phrase "essentially free," as used herein, refers to an amount less than or equal to 0.5, 0.1, 0.05 or 0.01 wt. %.

Additional Sunscreen Active Agents

The compositions of the subject present disclosure may optionally contain another sunscreen active agent in combination with the polyhydroxy fullerene. As used herein, "sunscreen active" includes both sunscreen agents and physical sunblocks. Suitable sunscreen actives may be organic or inorganic.

A wide variety of conventional organic or inorganic sunscreen actives are suitable for use herein. In one embodiment, the composition comprises from about 0.1% to about 20%, more typically from about 0.5% to about 10% by weight of the composition, of the sun screen active. Exact amounts will vary depending upon the sunscreen chosen and the desired Sun Protection Factor (SPF).

As examples of organic sunscreen agents which are active in UV-A and/or UV-B, there may be mentioned in particular those designated below by their CTFA name: para-aminobenzoic acid derivatives: PABA, Ethyl PABA, Ethyl Dihydroxypropyl PABA, Ethylhexyl Dimethyl PABA sold in particular under the name "ESCALOL 507" by ISP, Glyceryl PABA, PEG-25 PABA sold under the name "UVINUL P25" by BASF, salicyclic derivatives: Homosalate sold under the name "EUSOLEX HMS" by RONAIEM INDUSTRIES, Ethylhexyl Salicylate sold under the name "NEO HELIOPAN OS" by HAARMANN and REIMER, Dipropyleneglycol Salicylate sold under the name "DIPSAL" by SCHER, TEA Salicylate, sold under the name "NEO HELIOPAN TS" by HAARMANN and REIMER, and Octisalate, dibenzoylmethane derivatives: Butyl Methoxydibenzoylmethane sold in particular under the trademark "PARSOL 1789" by HOFFMANN LA ROCHE, Isopropyl Dibenzolylmethane, cinnamic derivatives: Ethylhexyl Methoxycinnamate sold in particular under the trademark "PARSOL MCX" by HOFFMANN LA ROCHE, Isopropyl Methoxy Cinnamate, Isoamyl Methoxy Cinnamate sold under the trademark "NEO HELIOPAN E 1000" by HAARMANN and REIMER, Cinoxate, DEA Methoxycinnamate, Diisopropyl Methylcinnamate, Glyceryl Ethylhexanoate Dimethoxycinnamate, β,β'-diphenylacrylate derivatives: Octocrylene sold in particular under the trademark "UVINUL N539" by BASF, Etocrylene, sold in particular under the trademark "UVINUL N35" by BASF, benzophenone derivatives: Avonbenzone, Benzophenone-1 sold under the trademark "UVINUL 400" by BASF, Benzophenone-2 sold under the trademark "UVINUL D50" by BASF, Benzophenone-3 or Oxybenzone, sold under the trademark "UVINUL M40" by BASF, Benzophenone-4 sold under the trademark "UVINUL MS40" by BASF, Benzophenone-5, Benzophenone-6 sold under the trademark "HELISORB 11" by NORQUAY, Benzophenone-8 sold under the trademark "SPECTRA-SORB UV-24" by AMERICAN CYANAMID, Benzophenone-9 sold under the trademark "UVINUL DS-49" by BASF, Benzophenone-12, benzylidene camphor derivatives: Ecamsule, 3-Benzylidene Camphor, 4-Methylbenzylidene Camphor sold under the name "EUSOLEX 6300" by MERCK, Benzylidene Camphor Sulphonic Acid, Camphor Benzalkonium Methosulphate, Terephthalylidene Dicamphor Sulphonic Acid, Polyacrylamidomethyl Benzylidene Camphor, phenylbenzimidazole derivatives: Phenylbenzimidazole Sulphonic Acid sold in particular under the trademark "EUSOLEX 232" by MERCK, Benzimidazilate sold under the trademark "NEO HELIOPAN AP" by HAARMANN and REIMER, triazine derivatives: Anisotriazine sold under the trademark "TINOSORB S" by CIBA GEIGY, Ethylhexyl triazones sold in particular under the trademark "UVINUL T150" by BASF, Diethylhexyl Butamido Triazone sold under the trademark "UVASORB HEB" by SIGMA 3V, phenylbenzotriazole derivatives: Drometrizole Trisiloxane sold under the name "SILATRIZOLE" by RHODIA CHIMIE, anthranilic derivatives: Menthyl anthranilate sold under the trademark "NEO HELIOPAN MA" by HAARMANN and REIMER, imidazoline derivatives: Ethylhexyl Dimethoxybenzylidene Dioxoimidazoline Propionate, benzalmalonate derivatives: Polyorganosiloxane with benzalmalonate functional groups sold under the trademark "PARSOL SLX" by HOFFMANN LA ROCHE, and mixtures thereof. others: dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); uric and violuric acids; tannic acid and its derivatives (e.g., hexaethylether); (butyl carbotol) (6-propyl piperonyl)ether; hydroquinone.

Organic non-PHF sunscreen agents which are more particularly preferred are chosen from the following compounds: Ethylhexyl Salicylate, Butyl Methoxydibenzoylmethane, Ethylhexyl Methoxycinnamate, Octocrylene, Phenylbenzimidazole Sulphonic Acid, Terephthalylidene Dicamphor Sulphonic, Benzophenone-3, Benzophenone-4, Benzophenone-5,4-Methylbenzylidene camphor, Benzimidazilate, Anisotriazine, Ethylhexyl triazone, Diethylhexyl Butamido Triazone, Methylene bis-Benzotriazolyl Tetramethylbutylphenol, Drometrizole Trisiloxane, and mixtures thereof. In some embodiments, the organic sunscreen agents include PABA and its derivatives, such as 2-Ethylhexyl p-dimethylamino-benzoate, Octinoxate, Camphor derivatives, such as 3-(4"Trimethylammonium)-benzyliden-bornan-2-on-methylsulfate, Octocrylene, Octylsalicylate (Octisalate), Benzophenone-3 (Oxybenzone), Benzophenore-4 or 8, Avobenzone, Ecamsule, Silatrizol, and Homosalate.

The inorganic sunscreen agents which may be used in the composition according to the present disclosure are particles of coated or uncoated metal oxides such as for example nanopigments of titanium oxide (amorphous or crystallized in the form of rutile and/or anatase), iron, zinc, zirconium or cerium oxides and mixtures thereof. Coating agents are moreover alumina, silica, and/or aluminum stearate. Such nanopigments of metal oxides, coated or uncoated, are in particular described in EP-A-0-518,772 and EP-A-0-518, 773. One preferred $TiO_2/ZnO_2$ sunscreen agent is OPTI-SOL, proposed by Oxonica When used herein, the inorganic sunscreens are present in the amount of from about 0.01% to about 20%, preferably from about 0.1% to about 10%, more preferably from about 1% to about 5%, by weight of the composition.

Anti-Oxidants/Radical Scavengers

In some embodiments, the sunscreen compositions can include an anti-oxidant/radical scavenger. In one embodiment, the composition comprises from about 0.01% to about 10%, more preferably from about 0.1% to about 5%, of an anti-oxidant/radical scavenger.

Anti-oxidants/radical scavengers such as retinyl palmitate, ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, Vitamin B compounds, N-acetyl-D-glucosamine, glucosyl hesperidin, hexamidine compounds, ascorbyl glucoside, palmitoyl-lysine-threonine-threonine-lysine-serine, butylated hydroxytoluene, cetyl betaine, bisabolol, theophylline, undecenoyl phenylalanine, cetyl pyridinium chloride, dihydroxyacetone, panthenol, butyl methoxydibenzoylmethane, glycyrrhizic acid, glycyrrhetinic acid, butylated hydroxyanisole, tetrahydrocurcumin, ergothioneine, octadecenedioic acid, retinyl propionate, yeast extract, Metalloenzymes, such as superoxide dismutase, perborate, thioglycolates, persulfate salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, amines (e.g., N,N-diethylhydroxylamine, amino-guanidine), nordihydroguaiaretic acid, bioflavonoids, sulfhydryl compounds (e.g., glutathione), dihydroxy fumaric acid and its salts, lysine pidolate, arginine pilolate, amino acids, silymarin, lysine, 1-methionine, proline, superoxide dismutase, sorbic acids and its salts, lipoic acid, olive extracts, tea extracts, polyphenols such as proanthocyanidine from pine bark, carotenoids, curcumin compounds such as tetrahydrocurcumin, OCTA (L-2-oxo-4-thiazolidine carboxylic acid), glutathione, melanin, green tea extracts, rosemary extracts and grape skin/seed extracts may be used.

Antioxidants which are more particularly preferred are chosen from the following compounds: Vitamins, such as vitamin E, K and C; Polyphenols, such as green tea polyphenols; Flavonoids; Catechins; Salicyclic acid derivatives, such as Homosalate and Octisalate; and Epigallocatechin gallate (EGCG).

Encapsulation

In some embodiments, the polyhydroxy fullerene, alone or in combination with other active ingredients and antioxidants, can be encapsulated in polymeric or inorganic matrices and combination of polymeric and inorganic matrices. The encapsulation can be core-shell structure with PHF in the core or the PHF can be dispersed in the matrix of the encapsulating material. Encapsulation can be used to provide more controlled release and/or increased stability. Some examples of polymeric matrices are polylactic acid (PLA); polyglycolic acid (PGA); poly (lactic-co-glycolic) acid (PLGA); polyethylene glycol (PEG); polystyrene (PS); polycaprolactone (PCL); poly methyl methacrylate (PMMA); polyvinyl alcohol (PVA); Polyvinylpyrrolidone (PVP); Eudragit polymers; cellulose and chitosan. Some examples of inorganic matrices are silica, titanium dioxide, zinc oxide, vanadium oxide, tungsten oxide, cerium oxide, and a combination of these.

Additional Ingredients

In some embodiments, additional ingredients can be included in the sunscreen composition beyond the polyhydroxy fullerene and the dermatologically acceptable carrier. For example, the sunscreen composition can include a safe and effective amount of a conditioning agent selected from, for example, humectants, moisturizers, and skin conditioners. A variety of these materials can be employed and in one embodiment can be present at a level of from about 0.01% to about 20%, more preferably from about 0.1% to about 10%, and still more preferably from about 0.5% to about 7%, by weight of the composition. These materials can include, but are not limited to, guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, glycerol, hexanetriol, butanetriol, propylene glycol, butylene glycol, hexylene glycol and the like, polyethylene glycols, sugars (e.g., melibiose), starches, sugar and starch derivatives (e.g., alkoxylated glucose, fructose, glucosamine), hyaluronic acid, lactamide monoethanolamine, acetamide monoethanolamine, panthenol, allantoin, petroleum and mixtures thereof. Also useful herein are the propoxylated glycerols described in U.S. Pat. No. 4,976,953. Preferably, the conditioning agent is selected from urea, guanidine, sucrose polyester, panthenol, dexpanthenol, allantoin, glycerol, and combinations thereof.

Humectants can be selected from the group consisting of polyhydric alcohols, water soluble alkoxylated nonionic polymers, and mixtures thereof. Polyhydric alcohols useful herein include polyhydroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, PPG-12/SMDI copolymer and mixtures thereof.

In certain embodiments, the composition includes a pigment suitable for providing color or hiding power. The pigment suitable for providing color or hiding power may be composed of iron oxides, including red and yellow iron oxides, titanium dioxide, ultramarine and chromium or chromium hydroxide colors, and mixtures thereof. The pigment may be a lake pigment, e.g., an organic dye such as azo, indigoid, triphenylmethane, anthraquinone, and xanthine dyes that are designated as D&C and FD&C blues, browns, greens, oranges, reds, yellows, etc., precipitated onto inert binders such as insoluble salts. Examples of lake pigments include Red #6, Red #7, Yellow #5 and Blue #1. The pigment may be an interference pigment. Examples of interference pigments include those containing mica substrates, bismuth oxychloride substrates, and silica substrates, for instance mica/bismuth oxychloride/iron oxide pigments commercially available as CHROMALITE pigments (BASF), titanium dioxide and/or iron oxides coated onto mica such as commercially available FLAMENCO pigments (BASF), mica/titanium dioxide/iron oxide pigments including commercially available KTZ pigments (Kobo products), CELLINI pearl pigments (BASF), and borosilicate-containing pigments such as REFLECKS pigments (BASF).

The compositions of the present invention may further comprise one or more other cosmetically active agent(s). A "cosmetically active agent" is a compound that has a cosmetic or therapeutic effect on the skin, e.g., agents to treat wrinkles, acne, or to lighten the skin. The cosmetically active agent will typically be present in the composition of the invention in an amount of from about 0.001% to about 20% by weight of the composition, e.g., about 0.01% to about 10% such as about 0.1% to about 5% by weight of the composition.

Protection from Ultraviolet Light Using Polyhydroxy Fullerene Sunscreen Compositions The present invention includes methods of using the PHF sunscreen compositions described herein to protect a substrate (e.g., the skin of a subject) from damage caused by sunlight or other sources of ultraviolet radiation. The method includes use of any of the PHF sunscreen compositions described herein. Accordingly, in one aspect, the present invention provides a method of protecting a substrate from the effects of ultraviolet light, comprising administering an effective amount of a sunscreen composition comprising a dermatologically acceptable carrier and a fullerene compound according to the formula $C_{2n}(OH)_t(NH_2)_v(COOH)_w(COOM)_xO_yM_z$, wherein M is an alkali metal or alkaline earth metal, n is a number ranging from 10 to 270, t is number ranging from 0 to 60, v is a number ranging from 0 to 60, w is a number ranging from 0 to 60, x is a numbering ranging from 0 to 60, y is a number ranging from 0 to 30, and z is a number ranging from 0 to 30. In some embodiments, the substrate is the skin of a subject in need thereof.

In some embodiments, the substrate is the skin or hair of a subject. In other embodiments, the substrate is the surface of a plant, such as leaves or flowers, or the surface of a fruit. In other embodiments, the substrate is a non-living article. Examples of non-living articles include wood, paints, natural and man-made fibers, plastics, and other objects susceptible to damage by ultraviolet radiation.

Administration involves applying the sunscreen composition to the substrate. Topical administration is administration to the skin of a subject. The sunscreen composition can be applied manually, or using a device, and can be applied to a portion of the substrate (e.g., the skin of the subject), all of the substrate, or portions of the substrate that will be exposed to sunlight or another source of UV radiation (e.g., a welding arc). The best sunscreen protection is achieved by application 15 to 30 minutes before exposure, followed by one reapplication 15 to 30 minutes after exposure begins. Further reapplication is necessary only after activities such as swimming, sweating, and rubbing. The stated protection factor requires that 2 pt of sunscreen be applied per square centimeter of exposed skin. In some embodiments, topical administration is carried out only on a subject who is at risk of injury from sunlight or ultraviolet radiation. A subject can be at risk or in need thereof if they are planning on or expected to be exposed to sunlight or ultraviolet radiation, or a subject who has a condition that makes them particularly susceptible to injury from sunlight or ultraviolet radiation, such as being an albino or taking medication (e.g., some antibiotics, contraceptives, or tranquilizers) that causes increased sensitivity to sunlight.

As used herein, the term "protection" refers to a decrease in damage, tissue injury and/or symptoms of tissue injury resulting from exposure of a substrate (e.g., skin) to sunlight or other sources of damaging ultraviolet radiation. The decrease in damage or tissue injury and/or symptoms can vary in degree. For example, in some embodiments, the decrease is at least a 50% decrease, at least a 60% decrease, at least a 70% decrease, at least an 80% decrease, at least a 90% decrease, or a 100% decrease, which can also be referred to as prevention of injury. Tissue injury resulting from exposure to sunlight is also known as "sunburn." Typically, symptoms of sunburn include initial redness (erythema), followed by varying degrees of pain, proportional in severity to both the duration and intensity of exposure. Other symptoms can include edema, itching, peeling skin, rash, nausea, fever, chills, and syncope. The symptoms of sunburn represent a reaction of the body to DNA damage. Accordingly, protecting a subject from tissue injury from sunlight or other sources of UV radiation can also decrease the likelihood that the subject will develop cancer, and in particular skin cancer (e.g., melanoma).

Dermatologically Acceptable Carriers for Sunscreen Compositions

The sunscreen compositions of the present invention includes a dermatologically acceptable carrier that can be a liquid, lotion, ointment, cream, foam, scrub, gel, soap bar or toner. Non-limiting examples of such sunscreen compositions include leave-on skin lotions, creams, antiperspirants, deodorants, lipsticks, foundations, mascara, sunless tanners and sunscreen lotions and wash-off shampoos, conditioners, shower gels, toilet bars. In some cases, the sunscreen composition is clear. Also, the sunscreen composition may be a spray-on sunscreen composition.

The total amount of the polyhydroxy fullerene (and optionally other active sunscreen agents) can vary depending on the desired SPF and overall UV filtering strength of a final sunscreen composition. In one aspect, the total amount of the active agents in the sunscreen combination is about 50, 40, 30, 25, 20, 19, 18, 17, 16, 15, 14, 13, 12, 11, 10, 9, 8, 7, 6, 5, 4, 3, 2, 1, 0.5, or 0.1 wt. %.

In certain embodiments the sunscreen composition has a pH that is from about 4.0 to about 8.0, such as from about 5.5 to about 7.0.

The inventors have designed a model sunscreen to incorporate PHF that contains standard ingredients such as viscosity enhancers (HPMC), oils/emollients (cetyl alcohol), humectants (glycerin), gelling agents, film formers, and emulsifiers (Brij 99 and Brij 52). PHF is easily incorporated in the model formulation and provides uniform surface coverage. Additionally sustained release PHF containing particles for release over an 8 hour period may be added.

Oils/Emollients

Examples of oils/emollients that may be included in the sunscreen compositions include: hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and caprylyl glycol; synthetic esters and ethers, especially of fatty acids, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam oil, or the mixture of n-undecane ($C_{11}$) and of n-tridecane ($C_{13}$) sold under the reference Cetiol UT by the company Cognis; fluoro oils that are partially hydrocarbon-based and/or silicone-based, for instance those described in document JP-A-2 295 912; silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; mixtures thereof.

Additional examples include benzoic acid esters of $C_9$-$C_{15}$ alcohols, isononyl iso-nonanoate, $C_{12}$-$C_{15}$ alkyl benzoate, or any combinations thereof.

Specific examples of oils/emollients include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of $C_9$-$C_{15}$ alcohols, isononyl iso-nonanoate, alkanes, mineral oil, silicone, dimethyl polysiloxane, ether, polyoxypropylene butyl ether, polyoxypropylene cetyl ether, $C_{12}$-$C_{15}$ alkyl benzoate, aryl alkyl benzoate, Isopropyl Lauroyl sarcosinate, and any combinations thereof.

Examples of hydrophilic organic solvents that may be included in the sunscreen compositions include: monohydric $C_1$-$C_8$ alcohols such as ethanol, propanol, butanol, isopropanol, isobutanol; Polyethylene glycols from 6 to 80 ethylene oxides such as propylene glycol, isoprene glycol, butylene glycol, glycerol, sorbitol; and mono or di-alkyl isosorbides such as dimethyl isosorbide.

Examples of amphiphilic organic solvents include: polypropylene glycol (PPG) like propylene glycol alkyl ester or alkyl ether of PPG like PPG-23 oleyl ether and PPG-36 oleate.

The total amount of oils/emollient present in the compositions is typically about 0.1, 0.5, 1.0, or 2.5 wt. % to about 5.0, 7.5, 10.0, 15.0, 20.0, or 30 wt. % of the total weight of the composition.

Film Formers

Film-formers are often incorporated into sunscreen compositions to ensure even coverage of the UV filters and can be used to render the composition water resistant. The film former is typically a hydrophobic material that imparts film forming and/or waterproofing characteristics. One such agent is polyethylene, which is available from New Phase Technologies as Performalene® 400, a polyethylene having a molecular weight of 400. Another suitable film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/$C_{12}$-$C_{22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, *Brassica campestris/aleuritis* Fordi Oil copolymer, decamethyl cyclopentasiloxane (and) trimethylsiloxysilicate, and mixtures thereof. In some cases, the film former is acrylates/$C_{12}$-$C_{22}$ alkylmethacrylate copolymer sold under the tradename Allianz OPT® by ISP.

Many of the common film-forming polymers included in sunscreen compositions are not soluble in ethanol (such as PVP/Eicosene copolymer). A common film-former employed in ethanol based sunscreen products is Dermacryl LT or Dermacryl 79 marketed by Akzo Nobel (INCI Name: acrylates/octylacrylamide copolymner). Dermacryl LT (CAS Number: 80570-62-3) is a hydrophobic, high molecular weight carboxylated acrylic copolymer. It functions as a film-former in a broad range of cosmetic formulations, imparting waterproofing, increased occlusivity and decreased rub-off of actives.

The total amount of film-formers present in the compositions is typically in an amount of about 0.1, 0.5, 1.0, or 5 wt. % to about 5, 10, 20, or 25 wt. %, based on the total weight of the composition.

Emulsifiers

The sunscreen compositions typically include at least one emulsifier such as an amphoteric, anionic, cationic or nonionic emulsifier, used alone or as a mixture, and optionally a co-emulsifier. The emulsifiers are chosen in an appropriate manner according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt. A crosslinked elastomeric solid organopolysiloxane comprising at least one oxyalkylene group, such as the product sold under the reference KSG 21 by the company Shin-Etsu, may also be used as surfactants for W/O emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The fatty acid esters of a sugar that can be used as nonionic amphiphilic lipids can be chosen in particular from the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose.

The $C_5$-$C_{22}$ or $C_{14}$-$C_{22}$ fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the disearate of methylglucose and of polyglycerol-3, sold by the company Goldschmidt under the name Tego-care 450. Mention may also be made of glucose monoesters or maltose monoesters, such as methyl O-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a $C_5$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers that can be used in the emulsion of the instant disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tego-care CG90 by the company Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure. These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units. These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span 60, sorbitan monopalmitate (CTFA name: sorbitan palmitate) sold by the company ICI under the name Span 40, or sorbitan 20 EO tristearate (CTFA name: polysorbate 65) sold by the company ICI under the name Tween 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl. By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BBS, BB10, BB20 and BB30 by the company Nikko, and the ether of stearyl alcohol comprising 2 ethylene oxide units (CTFA name: steareth-2), such as the product sold under the name Brij 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic L81 of formula (V) with x=z=6, y=39 (HLB 2); Poloxamer 282, such as the product sold by the company ICI under the name Pluronic L92 of formula (V) with x=z=10, y=47 (HLB 6); and Poloxamer 124, such as the product sold by the company ICI under the name Pluronic L44 of formula (V) with x=z=11, y=21 (HLB 16).

Suitable hydrophobically-modified emulsifiers include, for example, inulin lauryl carbamate, commercially available from Beneo Orafti under the tradename Inutec SP1.

The total amount of emulsifier present in the compositions is typically in an amount of about 0.1, 0.2, or 0.5 wt. % to about 4.0, 5.0, 6.0, or 7.5 wt. %, based on the total weight of the composition.

Gelling Agent

Gelling agents may also be included in the sunscreen compositions. Examples of suitable hydrophilic gelling agents include beeswax, carboxyvinyl polymers such as the Carbopol products (carbomers) and the Pemulen products (acrylate/C10-C30-alkylacrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, which are optionally crosslinked and/or neutralized, for instance the poly(2-acrylamido-2-methylpropanesulfonic acid) (CTFA name: ammonium polyacryldimethyltauramide); cellulose-based derivatives such as hydroxyethyl-cellulose and hydroxypropyl methyl cellulose; polysaccharides and especially gums such as xanthan gum or Arabic gum; and mixtures thereof.

Lipophilic gelling agents (thickeners) that may be mentioned include modified clays such as hectorite and its derivatives, for instance the products sold under the name bentone.

In some instances, the gelling agent is ammonium acryloyldimethyltaurate/steareth-25 methacrylate crosspolymer, commercially available from Clariant under the tradename Aristoflex HMS.

The gelling agent is typically used in an amount of about 0.05 to about 1.5% by weight, from about 0.08 to about 1.0% by weight, or about 0.1 to about 0.5% by weight, based on the total weight of the composition.

Examples of dermatologically acceptable carriers for polyhydroxy fullerenes that have been specifically tested by the inventors include: Hydroxy propyl methyl cellulose (HPMC) (5%); Sodium stearate (0.5%); Glycerin (5-30%); Edible oils including coconut oil and olive oil; Water-in-oil emulsion; Polyethylene glycol (5-50%); Brij 99 (0.01-10%); Collagen; HPMC (1-5%)+Glycerin (1-25%); Beeswax (0-5%)+HPMC (0-10%)+Brij 99 (0-5%)+Stearic acid (0-5%)+PHF (0.1-10%)+Cetyl alcohol (0-5%)+Stearyl alcohol (0-5%)+Glycerin (0-10%)+Isopropyl palmitate (0-5%)+Brij 52 (0-5%)+Glycerin trioctanoate (0-5%)+Deionized water (to total 100%); and Xanthan gum (0-10%)+Stearic acid (0-25%)+$K_2CO_3$ (0-2%)+NaOH (0-2%)+Glycerin (0-30%)+PHF (0.1-10%)+Deionized water (to total 100%).

The present invention is illustrated by the following examples. It is to be understood that the particular examples, materials, amounts, and procedures are to be interpreted broadly in accordance with the scope and spirit of the invention as set forth herein.

EXAMPLES

Example 1: Comparison of PHF with Conventional Sunscreen Compositions

Figure 2:
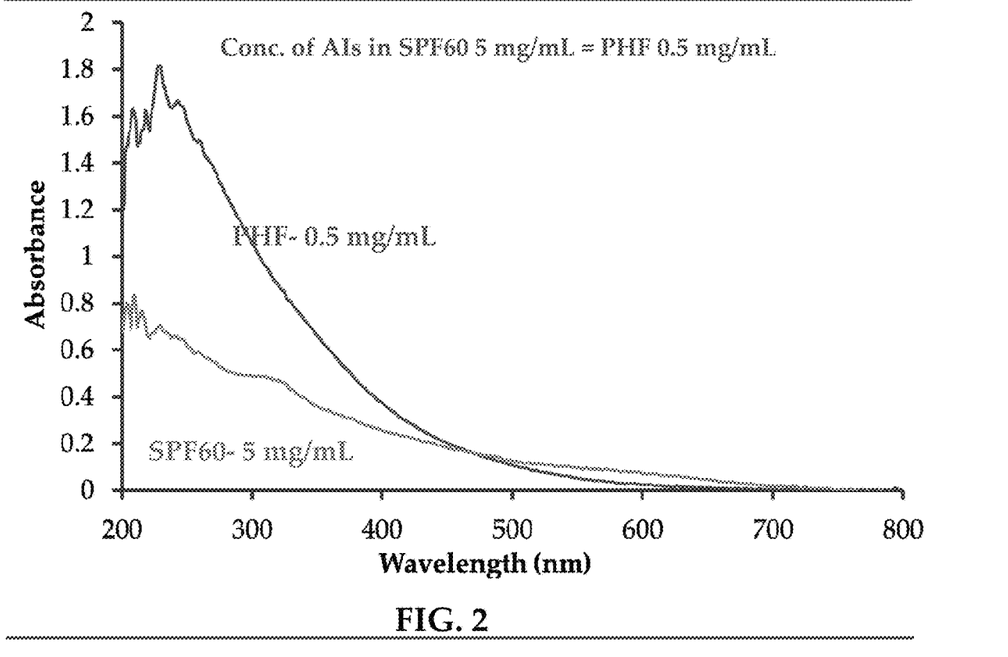
FIG. 2 provides a graph showing the UV-Visible absorbance spectra for a commercial SPF60 sunscreen formulation and PHF solution.
Figure 3:
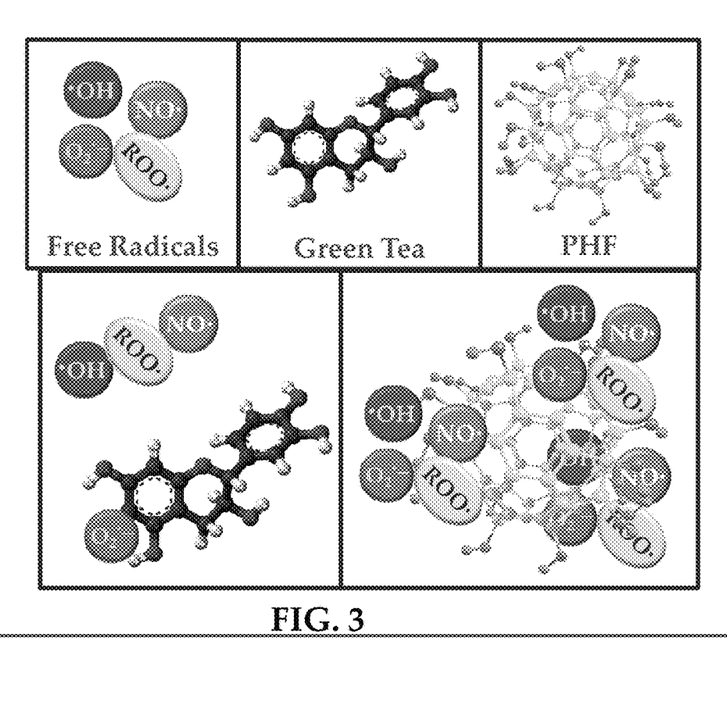
FIG. 3 provides images showing how polyhydroxy fullerene (PHF) molecules can neutralize different types and multiple numbers of free radicals compared to natural antioxidants such as green tea catechin, which can scavenge only one free radical.

The inventors discovered that PHF absorbs UV more effectively than commercial sunscreens. For initial comparisons (FIG. 2), the UV-Vis absorption of PHF solution at 0.5 mg/mL (prepared in 25% glycerol) was compared with Neutrogena SPF 60 (4.9% Titanium dioxide and 4.7% Zinc oxide) sunscreen at 5 mg/mL (in de-ionized water). The total concentration of AI in the commercial sunscreen suspension was equal to that of PHF (0.5 mg/mL) solution. PHF is a broad spectrum UV absorber, as its critical wavelength of 381 nm and UVA/UVB ratio of 1.6 exceeds the FDA limit of 370 nm and 0.91, respectively. The absorbance of PHF is 2.5-1.9 times higher in the UVB region (280-320 nm) and 1.9-1.5 times higher in the UVA region (320-400 nm) than SPF60 sunscreen. This high UV absorptive ability of PHF (for preventing direct damage from UVB and UVA) becomes even more important when combined with other potential advantages of PHF (preventing indirect free radical mediated damage) over current sunscreen AIs, as summarized in Table 1 and FIG. 3.

TABLE 1

Advantages and limitations of actives used in sunscreen formulations and comparison with proposed polyhydroxy fullerene based sunscreens.

| Properties | Inorganic UV absorbers | Organic UV absorbers | Polyhydroxy Fullerenes |
|---|---|---|---|
| UVB absorption (280-320 nm) | $TiO_2$, ZnO | Octocrylene, Octinoxate, Octisalate, Homosalate, etc. | PHF |
| UVA absorption (320-400) | ZnO, $TiO_2$ | Avobenzone, Oxybenzone, etc. | PHF |
| Stabilizers | Not needed | Octocrylene, Oxybenzone, Homosalate, etc. | Not needed |
| Antioxidants | Can be degraded; rarely used* | Homosalate, Vitamin C, Vitamin E, EGCG, etc. | PHF |
| Potential ROS generation | $TiO_2$, ZnO* | Octocrylene, Oxybenzone, etc.* | None |
| Photolabile | No | Avobenzone, Octinoxate, Octisalate, etc.* | No |
| ROS susceptibility | None* | Yes* | Catalytically neutralizes ROS |
| Phototoxicity potential | Less* | High, depending on the AI* | Not expected |
| Safety concerns | Low* | High* | Not expected |

Items that include an asterix* indicate limitations.

Example 2: In Vivo Experiments

Figures 4A, 4B, 4C, 4D, 4E, 4F:
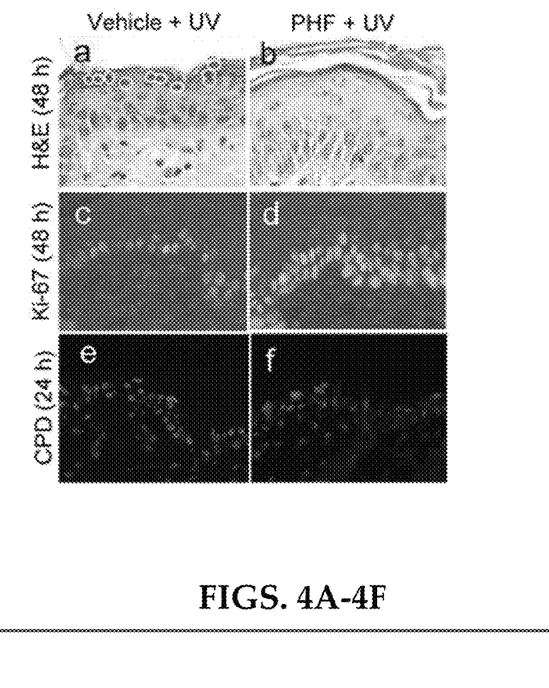
FIGS. 4A-4F provide images showing the ability of PHF to absorb UV and prevent damage to the skin, in a murine model. Histological analysis with standard H&E staining (a-b), or immunofluorescent staining with anti-Ki-67 to assess proliferation (c, d) or anti-CPD (e, f) to assess DNA damage and rate of photoproduct removal. White circles in a, b; apoptotic sunburn cells.

The inventors preliminary data show that PHF is not only effective in blocking UVB transmission in vitro (FIG. 2), but also in reducing damage to the skin in vivo (FIG. 4). In vivo experiments were carried out with hairless S K H-1 mice, a standard model for studying UV damage (Anand et al., J Invest Dermatol, 2005. 125(2): p. 323-33) and carcinogenesis (Kim et al., PLoS One, 2012. 7(6): p. e39691) in the skin. FIG. 4 shows data from initial experiments to examine PHF's effects upon UV-inducible biomarkers in living mouse skin. PHF (obtained from MER Corp.) was dissolved in water and applied on the right flank (2 cm×1 cm) of the dorsal region of hairless SKH-1 mice. The left flank (2 cm×1 cm) of the same mouse was used as a control with topical application of deionized water. The topical applications were allowed to dry for 15 minutes followed by UV exposure (80 mJ/cm$^2$; 90% UVB and 10% UVA). At 24 hours after UV exposure, the flanks of mice were observed for redness or erythema. PHF treated regions did not show any signs of erythema (sunburn), whereas control flanks were red indicating severe sunburn. Mice were euthanized 48 hours post-UV exposure, and the skin was harvested for histological analysis or immunofluorescent staining. Histological analysis of the skin showed (i) a marked reduction in epidermal cell death (dyskeratotic "sunburn cells"), compare FIGS. 4a and 4b; (ii) faster recovery of proliferation (cell division occurring 24-48 h after UVB), compare FIGS. 4c and 4d; and (iii) fewer DNA photoproducts (cyclopyrimidine dimers, CPD's) observed in skin treated with PHF, compare FIGS. 4e and 4f.

Example 3: PHF Formulation

Figure 5:
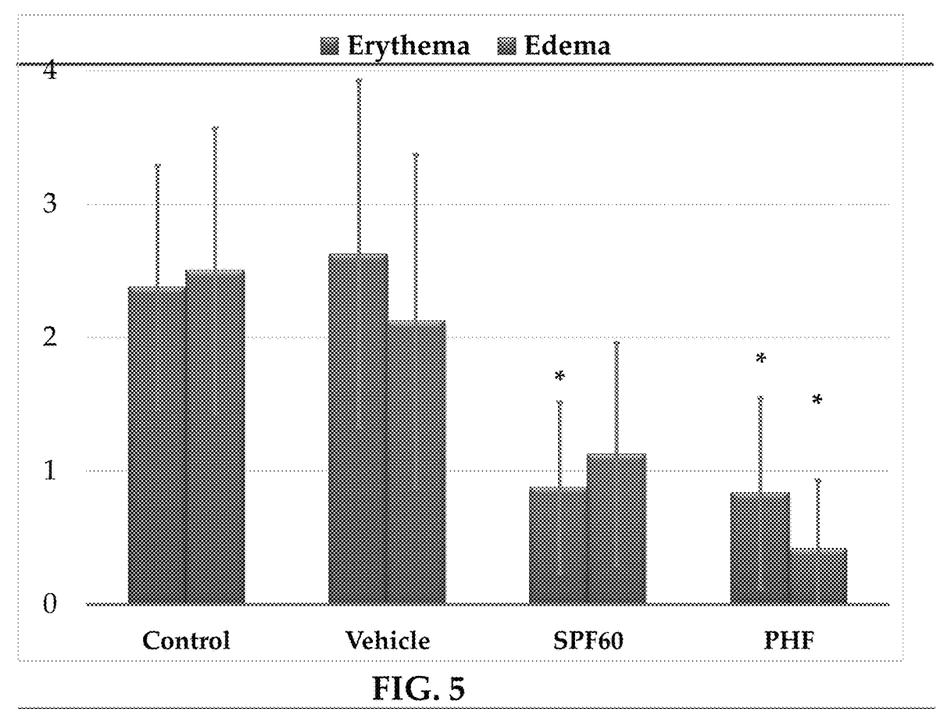
FIG. 5 provides a graph showing a comparison of blinded scoring for 48 hour erythema and edema of skin sections with different topical applications. *indicates significance at α=0.01 as compared to control.

PHF is a single, multifunctional active that replaces multiple actives of current sunscreen formulations. A suitable vehicle for PHF was designed that does not compromise the rheological properties required for topical application of sunscreen. The concentration of PHF was optimized and the minimum concentration of PHF that prevents symptoms of sunburn (erythema and edema) was determined. In a preclinical model, different skin sections were applied with PHF formulation, SPF60 commercial sunscreen, vehicle (without PHF) samples and control (no application). All skin sections were exposed to UVB at 120 mJ/cm$^2$ dose. The skin sections were monitored for erythema (redness) and edema (swelling) at 24, 48 and 72 hours. Maximum erythema is usually observed at 48 hours. The photographs of skin sections at 48 hours were scored by a panel consisting of two dermatologists and two non-dermatologists. The panel was blinded to the identity of the samples. The scale used for scoring is shown in Table 2. The result of blinded scoring study is plotted in FIG. 5. PHF reduced erythema and edema significantly ($\alpha=0.01$) compared to control and vehicle only formulations, and was on par with commercial SPF60 sunscreen.

TABLE 2

Scale for scoring erythema and edema of skin
SKIN REACTIONS

| | SCORE |
|---|---|
| Erythema and eschar formation | |
| None | 0 |
| Barely perceptible | 1 |
| Slight erythema (well-defined edges, pink throughout the exposed area) | 2 |
| Moderate erythema | 3 |
| Severe erythema (Beet red) with some ulceration | 4 |
| Edema formation | |
| None | 0 |
| Barely perceptible | 1 |
| Slight erythema (well-defined edges, pink throughout the exposed area) | 2 |
| Moderate edema (raised ~1 mm) | 3 |
| Severe edema (raised >1 mm) | 4 |

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A sunscreen composition, comprising a dermatologically acceptable carrier and a polymer-bearing fullerene compound according to the formula $C_{2n}[C_mO_pH_q](OH)_t(COOH)_w(COOM)_xO_yM_z$, wherein M is an alkali metal, alkaline earth metal, transition metal, post-transition metal, or lanthanide, n is a number ranging from 10 to 270, m is a number ranging from 1 to 30, p is a number ranging from 0 to 15, q is a number ranging from 2 to 60 t is number ranging from 8 to 60, w is a number ranging from 0 to 60, x is a number ranging from 0 to 60, y is a number ranging from 0 to 30, and z is a number ranging from 0 to 30.

2. The sunscreen composition of claim 1, wherein the sunscreen composition further comprises an antioxidant.

3. The sunscreen composition of claim 1, wherein the polymer-bearing fullerene compound is an endohedral fullerene comprising a rare earth metal compound.

* * * * *